US006677320B2

(12) United States Patent
Diederich et al.

(10) Patent No.: US 6,677,320 B2
(45) Date of Patent: Jan. 13, 2004

(54) PARENTERAL BISPHOSPHONATE COMPOSITION WITH IMPROVED LOCAL TOLERANCE

(75) Inventors: Anke Diederich, Basel (CH); Pierre Goldbach, Rixheim (FR); Thomas Pfister, Sissach (CH)

(73) Assignee: Hoffmann-La Roches Inc., Nutley, NJ (US)

( * ) Notice: Subject to any disclaimer, the term of this patent is extended or adjusted under 35 U.S.C. 154(b) by 49 days.

(21) Appl. No.: 09/758,605

(22) Filed: Jan. 11, 2001

(65) Prior Publication Data

US 2001/0011082 A1 Aug. 2, 2001

(30) Foreign Application Priority Data

Jan. 20, 2000 (EP) ............................... 00101044

(51) Int. Cl.[7] .............................................. A61K 31/66
(52) U.S. Cl. ...................... 514/102; 514/103; 514/104; 514/107; 514/108
(58) Field of Search ................ 514/102, 103, 514/104, 107, 108

(56) References Cited

U.S. PATENT DOCUMENTS

| | | | |
|---|---|---|---|
| 3,962,432 A | 6/1976 | Schmidt-Dunker | 424/204 |
| 4,054,598 A | 10/1977 | Blum et al. | 260/502.5 |
| 4,252,742 A | 2/1981 | Blackwell, III et al. | 564/447 |
| 4,267,108 A | 5/1981 | Blum et al. | 260/326.61 |
| 4,327,039 A | 4/1982 | Blum et al. | 260/502.5 |
| 4,407,761 A | 10/1983 | Blum et al. | 260/502.5 |
| 4,621,077 A | 11/1986 | Rosini et al. | 514/108 |
| 4,624,947 A | 11/1986 | Blum et al. | 514/108 |
| 4,666,895 A | 5/1987 | Bosies et al. | 514/108 |
| 4,719,203 A | 1/1988 | Bosies et al. | 514/108 |
| 4,746,654 A | 5/1988 | Breliere et al. | 514/108 |
| 4,761,406 A | 8/1988 | Flora et al. | 514/86 |
| 4,777,163 A | 10/1988 | Bosies et al. | 514/80 |
| 4,784,993 A | 11/1988 | Bosies et al. | 514/93 |
| 4,876,248 A | 10/1989 | Breliere et al. | 514/108 |
| 4,886,499 A | 12/1989 | Cirelli et al. | 604/131 |
| 4,922,077 A | 5/1990 | Gordon | 219/121.68 |
| 4,927,814 A | 5/1990 | Gall et al. | 514/108 |
| 4,942,157 A | 7/1990 | Gall et al. | 514/108 |
| 4,970,335 A | 11/1990 | Isomura et al. | 562/13 |
| 4,971,958 A | 11/1990 | Bosies et al. | 514/89 |
| 5,002,937 A | 3/1991 | Bosies et al. | 514/108 |
| 5,019,651 A | 5/1991 | Kieczykowski | 562/13 |
| 5,616,571 A * | 4/1997 | Daifotis et al. | 514/102 |
| 5,730,715 A * | 3/1998 | Sage, Jr. et al. | 604/20 |

FOREIGN PATENT DOCUMENTS

| | | |
|---|---|---|
| DE | 42 44 422 | 6/1994 |
| DE | 42 44 423 | 6/1994 |
| EP | 022 751 | 1/1981 |
| EP | 170 228 | 2/1986 |
| EP | 0 203 649 | 3/1986 |
| EP | 197 478 | 10/1986 |
| EP | 252 504 | 1/1988 |
| EP | 252 505 | 1/1988 |
| EP | 258 618 | 3/1988 |
| EP | 273 190 | 7/1988 |
| EP | 350 002 | 1/1990 |
| EP | 449 405 | 10/1991 |
| WO | WO 90/00798 | 1/1990 |
| WO | WO 95/31203 | 11/1995 |
| WO | WO 96/05842 A1 * | 2/1996 |
| WO | WO 01/28555 | 4/2001 |

OTHER PUBLICATIONS

Abstract of Japanese Patent 080922102.
Quimby et al., J. Org. Chem., vol. 32, pp. 4111–4114 (1967).
Abstract for B2.
Abstract for B3.
Abstract for B5.
Abstract for B7.

* cited by examiner

*Primary Examiner*—Theodore J. Criares
*Assistant Examiner*—Jennifer Kim
(74) *Attorney, Agent, or Firm*—George W. Johnston; Patricia S. Rocha-Tramaloni; Bernard Lau (57) ABSTRACT

The present invention relates to a parenteral composition comprising a bisphosphonic acid or a pharmaceutically acceptable salt thereof (bisphosphonate) as active component and a pharmaceutically acceptable chelating agent, processes of the preparation of this composition, and methods of their use in the treatment and prevention of diseases involving bone resorption, especially osteoporosis, Paget's disease, hypercalcemia of malignancy, and metabolic bone disease. The compositions are especially useful for improving the local tolerance of the active component when administered parenterally.

2 Claims, 4 Drawing Sheets

PARENTERAL BISPHOSPHONATE COMPOSITION WITH IMPROVED LOCAL TOLERANCE

BACKGROUND OF THE INVENTION

The present invention relates to a parenteral composition comprising a bisphosphonic acid or a pharmaceutically acceptable salt thereof (bisphosphonate) as active component, a pharmaceutically acceptable chelating agent and pharmaceutically acceptable excipients, processes of the preparation of this composition, and methods of their use in the treatment and prevention of diseases involving bone resorption, especially osteoporosis, Paget's disease, hypercalcemia of malignancy, and metabolic bone disease. The compositions are especially useful for improving the local tolerance of the active component when administered parenterally, especially by the subcutaneous route.

Bisphosphonates, i.e. bisphosphonic acids or soluble, pharmaceutically acceptable salts thereof, are synthetic analogs of the naturally occurring pyrophosphate. Due to their marked affinity for solid-phase calcium phosphate, bisphosphonates bind strongly to bone mineral. Pharmacologically active bisphosphonates are well known in the art and are potent inhibitors of bone resorption and are therefore useful in the treatment and prevention of diseases involving abnormal bone resorption, especially osteoporosis, Paget's disease, hypercalcemia of malignancy, and metabolic bone disease.

Bisphosphonates as pharmaceutical agents are described for example in EP-A-170,228, EP-A-197,478, EP-A-22,751; EP-A-252,504, EP-A-252,505, EP-A-258,618, EP-A-350,002, EP-A-273,190, WO-A-90/00798, etc.

Pharmaceutical forms of marketed bisphosphonates are oral formulations (tablets or capsules) or solutions for intravenous injection or infusion. They are systemically well tolerated when administered at therapeutic doses. However, bisphosphonates as a class are irritant to skin and mucous membranes resulting in digestive tract side effects, e.g. esophageal adverse events or gastrointestinal disturbances. In consequence, the oral route of administration has to follow inconvenient recommendations of use for the patient. The intravenous route of administration is complicated by adverse events in case of application failure. If the vein is not exactly met or if the drug is administered inadvertently by the paravenous route, severe local tissue reaction are induced including necroses. Thus, there is a substantial need to improve the pharmaceutical formulation of bisphosphonates in order to reduce or avoid tissue damage after parenteral administration, especially by the subcutaneous route.

The pathophysiological mechanism of bisphosphonate induced tissue damage is unknown. As the local reactions are similar for different bisphosphonates, at least those induced by nitrogen-containing bisphosphonates (aminobisphosphonates), a common mechanism must be assumed. The delay in onset and progress of local reactions may indicate the involvement of the unspecific immune defense system.

Attempts were made to improve tissue tolerance of bisphosphonates by developing suspensions of insoluble or poorly soluble salts of bisphosphonates providing local sustained release, e.g. described in EP 449,405, DE-A-4244422 and DE-A-4244423. However, this approach proved to improve only slightly the local tolerance.

The problem underlying the present invention is therefore to provide a composition which is able to minimize or suppress the above mentioned disadvantages.

SUMMARY OF THE INVENTION

The problem is solved, according to the present invention, by a parenteral composition comprising a bisphosphonate and a pharmaceutically acceptable chelating agent.

It has surprisingly been found that administering a bisphosphonate in a composition comprising a pharmaceutically acceptable chelating agent clearly improves the duration, frequency and intensity of side effects. The presence of an additional bivalent cation chelator, especially EDTA and DTPA, substantially improved the adverse local reaction at the application sites when compared with the corresponding formulation without this additional bivalent cation chelator. A pharmaceutically acceptable excipient may also be added to the composition.

DETAILED DESCRIPTION OF THE INVENTION

Unless otherwise indicated the following definitions are set forth to illustrate and define the meaning and scope of the various terms used to describe the invention herein.

The term "bisphosphonate" means compounds characterised by two $C-PO_3^{2-}$ bonds. If the two bonds are located on the same carbon atom, the compounds are called geminal bisphosphonates. It should be noted that the term "bisphosphonate" as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated.

The term "chelating agent" or "chelator" means an organic or inorganic compound, which forms via two or more of its functional groups stable ring-shaped complexes with metal cations. It should be noted that bisphosphonates also have chelating activity. The term "chelating agent" is therefore understood to be a chelator which sequesters metal ions competitively to the bisphosphonate used as the active component in the pharmaceutical composition.

The term "pharmaceutically acceptable" as used herein means that the salts or chelating agents present a medically acceptable toxicity risk when administered to a patient according to established medical procedures.

The term "pharmaceutically acceptable salt" refers to ammonium salts, alkali metal salts such as potassium and sodium (including mono, di- and tri-sodium) salts (which are preferred), alkaline earth metal salts such as calcium and magnesium salts, salts with organic bases such as dicyclohexylamine salts, N-methyl-D-glucamine, and salts with amino acids such as arginine, lysine, and so forth.

The term "alkyl", alone or in combination, means a straight-chain, branched-chain, or cyclic alkyl group containing a maximum of 30, preferably a maximum of 10, and more preferably a maximum of 7, carbon atoms, e.g., methyl, ethyl, n-propyl, 2-methylpropyl (iso-butyl), 1-methylethyl (iso-propyl), n-butyl, 1,1-dimethylethyl (t-butyl), and pentyl. The term "alkyl" also comprises the above defined groups, optionally substituted with phenyl, pyridyl, furanyl, pyrrolidinyl, imidazolyl, amino, mono- or dialkylamino, hydroxy, SH, and alkoxy.

The term "diluent" means an ingredient in a medicinal preparation which lacks pharmacological activity but is pharmaceutically necessary or desirable. For example a diluent may be a liquid for the dissolution of drug(s) to be injected, e.g. water.

The term "solvents" refers to a liquid that holds another substance in solution, i.e., dissolves it, e.g. water.

The term "preservatives" refers to a substance added to a pharmaceutical preparation to prevent bacterial growth.

The term "device" means a contrivance for a specific purpose. In the present invention the purpose is to enable, support or facilitate parenteral drug administration.

The term "local anaesthetic" refers to a compound that reversibly depresses neuronal function at the site of application, producing loss of ability to perceive pain and/or other sensations, e.g. lidocaine hydrochloride.

In more detail, the present invention is directed to a parenteral composition comprising a bisphosphonate and a pharmaceutically acceptable chelating agent. The parenteral compositions may have the form of a liquid, e.g. an aqueous solution, or a sterile powder and/or lyophilisate. A liquid, e.g. water, may be added to the sterile powder and/or lyophilisate to give a solution for administration.

In a preferred embodiment of the present invention, the above composition is a liquid, preferably an aqueous solution.

Bisphosphonates as pharmaceutical agents are described for example in U.S. Pat. No. 4,666,895, U.S. Pat. No. 4,719,203, EP-A-252,504, EP-A-252,505, U.S. Pat. No. 4,777,163, U.S. Pat. No. 5,002,937 and U.S. Pat. No. 4,971,958.

Methods for the preparation of bisphosphonic acids may be found in, e.g., U.S. Pat. No. 3,962,432; U.S. Pat. No. 4,054,598; U.S. Pat. No. 4,267,108; U.S. Pat. No. 4,327,039; U.S. Pat. No. 4,407,761; U.S. Pat. No. 4,621,077; U.S. Pat. No. 4,624,947; U.S. Pat. No. 4,746,654; U.S. Pat. No. 4,922,077; U.S. Pat. No. 4,970,335; U.S. Pat. No. 5,019,651; U.S. Pat. No. 4,761,406; U.S. Pat. No. 4,876,248; J. Org. Chem. 32, 4111 (1967) and EP-A-252,504. The pharmaceutically acceptable salts of bisphosphonic acids may also be employed in the instant invention. Examples of base salts of bisphosphonic acids include ammonium salts, alkali metal salts such as potassium and sodium (including mono, di- and tri-sodium) salts (which are preferred), alkaline earth metal salts such as calcium and magnesium salts, salts with organic bases such as dicyclohexylamine salts, N-methyl-D-glucamine, and salts with amino acids such as arginine, lysine, and so forth. The non-toxic, physiologically acceptable salts are preferred. The salts may be prepared by methods known in the art, such as described in European Patent Pub. No. 252,504 or in U.S. Pat. No. 4,922,077.

In a preferred embodiment of the present invention, the term "bisphosphonate" of the present invention corresponds to compounds of formula (I)

wherein A and X are independently selected from the group consisting of hydrogen, hydroxy, halogen, amino, SH, phenyl, alkyl, mono- or dialkylamino, mono- or dialkylaminoalkyl, alkoxy, thioalkyl, thiophenyl, and aryl or heteroaryl moieties selected from the group consisting of phenyl, pyridyl, furanyl, pyrrolidinyl, imidazolyl, and benzyl, wherein the aryl or heteroaryl moiety is optionally substituted with alkyl.

In the foregoing chemical formula, A can include X and X include A such that the two moieties can form part of the same cyclic structure.

The foregoing chemical formula is also intended to encompass carbocyclic, aromatic and heteroaromatic structures for the A and/or X substituents, e.g. naphthyl, quinolyl, isoquinolyl, adamantyl, and chlorophenylthio.

Preferred structures are those in which A is selected from the group consisting of hydrogen, hydroxy, and halogen, an X is selected from the group consisting of alkyl, halogen, thiophenyl, thioalkyl and dialkylaminoalkyl.

More preferred structures are those in which A is selected from the group consisting of hydrogen, hydroxy, and Cl and X is selected from the group consisting of alkyl, Cl, chlorophenylthio and dialkylaminoalkyl.

Even more preferred structures refer to the above defined compounds with the proviso that alendronate is not included.

Most preferred is when A is hydroxy and X is (N-methyl-N-pentyl)amino-ethyl, i.e. ibandronate.

Examples of bisphosphonates, i.e. bisphosphonic acids and pharmaceutically acceptable salts thereof which may be employed as active ingredients in the instant invention include:

a) 4-amino-1-hydroxybutylidene-1,1-bisphosphonic acid (alendronate), b) N-methyl-4-amino-1-hydroxybutylidene-1,1-bisphosphonic acid, c) 4-(N,N-dimethylamino)-1-hydroxybutylidene-1,1-bisphosphonic acid, d) 3-amino-1-hydroxypropylidene-1,1-bisphosphonic acid (pamidronate), e) 3-(N-methyl-N-pentyl) amino-1-hydroxypropane-1,1-bisphosphonic acid (ibandronic acid), f) [3-(N-methyl-N-pentyl) amino-1-hydroxypropane-1,1-bisphosphonic acid, monosodium salt, monohydrate] (ibandronate), g) 1-hydroxy-3-(N-methyl-N-pentylamino)propylidene-1,1-bisphosphonic acid, h) 1-hydroxy-2-[3-pyridinyl]ethylidene-1,1-bisphosphonic acid (risedronate), i) 4-(hyroxymethylene-1,1-bisphosphonic acid) piperidine, j) cycloheptylaminomethylene-1,1-bisposphonic acid (cimadronate), k) 1,1-dichloromethylene-1,1-diphosphonic acid and the dissodium salt (clodronate), l) 1-hydroxy-3-(1-pyrrolidinyl)-propylidene-1,1-bisphosphonic acid (EB-1053), m) 1-hydroxyethane-1,1-diphosphonic acid (etidronic acid), n) 6-amino-1-hydroxyhexylidene-1,1-bisphosphonic acid (neridronate), o) 3-(dimethylamino)-1-hydroxypropylidene-1,1-bisphosphonic acid (olpadronate), p) [2-(2-pyridinyl)ethylidene]-1,1-bisphosphonic acid (piridronate), q) (4-chlorophenyl)thiomethane-1,1-diphosponic acid (tiludronate), r) 1-hydroxy-2-(1H-imidazol-1-yl)ethylidene-1,1-bisphosphonic acid (zolendronate).

s) [(cycloheptylamino)-methylene]-bisphosphonic acid (icadronate), and/or t) [1-Hydroxy-2imidazo-(1,2-a) pyridin-3-ylethylidene]-bisphosphonic acid and pharmaceutically acceptable salts thereof.

In a preferred embodiment of the invention, bisphosphonates may be selected from the group consisting of compounds b) to t) and pharmaceutically acceptable salts thereof.

Preferred are bisphosphonates selected from the group consisting of cimadronate, clodronate, tiludronate, etidronate, ibandronate, risedronate, piridronate, pamidronate, zolendronate and pharmaceutically acceptable salts thereof.

In a more preferred embodiment of the present invention, the bisphosphonate is 3-(N-methyl-N-pentyl) amino-1-hydroxypropane-1,1-bisphosphonic acid (ibandronic acid) or pharmaceutically acceptable salts thereof, or even more preferably 3-(N-methyl-N-pentyl) amino-1-hydroxypropane-1,1-bisphosphonic acid, monosodium salt, monohydrate.

The pharmaceutically chelating agent or chelator or a pharmaceutically acceptable salt thereof according to the present invention is a compound, which forms via two or more of its functional groups stable ring-shaped complexes with metal cations, e.g. preferably a polyacetic acid or a pharmaceutically acceptable salt thereof like EDTA and DTPA. Chelating agents are complexes, which unlike simple ligands, e.g. ferrocyanide ($Fe(CN)_6^{4-}$), which form complex salts by a single bond provided by a lone electron pair, are capable of forming more than one bond. Ethylene diamine, for example, is bidentate (two links), tripyridyl is tridentate (three) and ethylene diamine tetraacetic acid (EDTA) is hexadentate (six) which makes it particularly effective as a pharmaceutical chelating agent. One of the consequences of chelation is the formation of a cyclic structure which has high thermodynamic and thermal stability analogous to aromatic rings. Furthermore, the chelate complex is usually more stable than the ligand, since two bonds must rupture, and although one may break, reformation occurs before the other can. This is known as the chelate effect.

Preferably the chelating agent is a bivalent cation chelator and more preferably, the chelator is selected from the group consisting of ethylenediaminetetraacetic acid (EDTA), diethylenetriaminepentaacetic acid (DTPA), ethylene glycol-bis(β-aminoethyl ether)-tetraacetic acid (EGTA), N (hydroxyethyl) ethylenediaminetriacetic acid (HEDTA), nitrilotriacetic acid (NTA), triethanolamine, 8-hydroxyquinoline, citric acid, tartaric acid, phosphoric acid, gluconic acid, saccharic acid, thiodipropionic acid, acetonic dicarboxylic acid, lecithin, di(hydroxyethyl) glycine, phenylalanine, tryptophan, glycerin, sorbitol and pharmaceutically acceptable salts thereof.

More preferably the chelating agent is selected from the group consisting of EDTA, DTPA, citric acid, tartaric acid, phosphoric acid, gluconic acid or a pharmaceutically acceptable salt thereof and even more preferably the pharmaceutically chelating agent is EDTA and DTPA or a pharmaceutically acceptable salt thereof.

In a preferred embodiment of the present invention the molar ratio between the bisphosphonate and the pharmaceutically acceptable chelating agent is about 1:0.01 to about 1:500, more preferably about 1:0.1 to about 1:50, and even more preferably is about 1:10.

For example, a formulation containing 1 mg ibandronate/ml physiological saline adjusted to pH 7.4. EDTA was added to the ibandronate solution at a concentration range of 0.1 to 10 mg/ml. This corresponds to molar ibandronate to EDTA ratios of approximately 1:0.1 to 1:10. The improving effect of EDTA was shown to be dose-related. At the lowest ratio of 1:0.1 there was still some beneficial effect and at the highest ratio of 1:10, the local adverse reactions were still not completely abolished. Thus, much higher and lower molar ratios can be expected to be also useful to improve the local tolerance of parenterally administered bisphosphonate formulations. In addition, the effect of EDTA on alendronate induced local reaction as well as the efficacy of DTPA as chelating agent could also be demonstrated.

The composition as defined above may contain one or more additional pharmaceutically acceptable chelating agent (s) as defined above.

The excipients may be selected diluents, solvents and/or preservatives, e.g. water, alcohols, polyols, glycerine, and vegetable oils. The compositions according to the present invention may comprise one or more of these pharmaceutically acceptable excipients.

In a preferred embodiment of the present invention the composition as defined above may comprise a bisphosphonate or a pharmaceutically acceptable salt thereof, a pharmaceutically acceptable chelating agent, a tonicity agent (a tonicity adjusting agent as described below), a pH adjusting agent (i.e. acid, base, buffer as described below), and a solvent. Optionally these compositions may contain in addition a local anaesthetic.

In a more preferred embodiment of the present invention, the pH of the solution of the above defined compositions is in the range of 2–10, preferably 4–9, more preferably 6–8, and most preferably 7–8, e.g. about 7.4.

In an even more preferred embodiment of the present invention the above defined composition is a parenteral composition comprising a) 0.1–10 mg 3-(N-methyl-N-pentyl) amino-1-hydroxypropane-1,1-bisphosphonic acid, monosodium salt, monohydrate and b) 0.5–50 mg EDTA, $Na_2$, $2H_2O$.

For example, the above composition may comprise a) 0.1–10 mg 3-(N-methyl-N-pentyl) amino-1-hydroxypropane-1,1-bisphosphonic acid, monosodium salt, monohydrate;

b) 0.5–50 mg EDTA, Na$_2$, 2H$_2$O;
c) about 9.0 mg sodium chloride;
d) sodium hydroxide q.s. to about pH 7.4; and
e) water for injection q.s. to 0.5 or 1.0 ml.

In more detail, a parenteral composition may comprise about 1.125 mg ibandronate sodium salt, about 10 mg EDTA, Na$_2$, 2H$_2$O, about 9.0 mg sodium chloride, sodium hydroxide q.s. to pH 7.4 and water for injection q.s. to 1.0 ml.

Preferably, a parenteral composition may comprise about 1.125 mg ibandronate sodium salt, about 10 mg EDTA, Na$_2$, 2H$_2$O, about 5.78 mg lidocaine hydrochloride, about 9.0 mg sodium chloride, sodium hydroxide q.s. to pH 7.4 and water for injection q.s. to 1.0 ml.

Further, the invention includes a process for preparing a composition as defined above, comprising mixing at least one bisphosphonate with at least one pharmaceutically acceptable chelating agent and a pharmaceutically acceptable excipient.

The invention also comprises a process for preparing a composition as defined above by mixing at least one bisphosphonate with at least one pharmaceutically acceptable chelating agent and a local anaesthetic.

The compositions of the present invention are useful for the treatment and prevention of diseases involving bone resorption, especially osteoporosis, Paget's disease, hypercalcemia of malignancy, and metabolic bone disease. The invention further comprises a method for the treatment and prevention of diseases involving bone resorption, especially osteoporosis, Paget's disease, hypercalcemia of malignancy, and metabolic bone disease comprising the step of administering to a patient a composition as defined above.

The invention further includes devices for local and systemic sustained release comprising a composition as defined above.

In more detail, the composition as defined above may contain additional excipients selected from solvents and co-solvents (water for injection, ethanol, glycerol, propylene glycol, polyethylene glycol, different oils), solubilising, wetting, suspending, emulsifying or thickening agents (carboxymethylcellulose, Cremophore EL, desoxycholate sodium, gelatin, lecithin, polysorbate 20 and 80, poloxamer), antioxidants and reducing agents (ascorbic acid, bisulfite sodium, metabisulfite sodium), antimicrobial preservatives (benzyl alcohol, paraben propyl and methyl), buffers and pH adjusting agents (acetate, citrate, lactate, hydrochloric acid, sodium hydroxyde), bulking agents, protectants, and tonicity adjustors (sodium chloride, glucose, mannitol), or a local anesthetic (lidocaine, benzocaine, buvicaine, procaine, tetracaine).

In a preferred embodiment of the present invention the composition is a parenteral composition comprising a bisphosphonate and a pharmaceutically acceptable chelating agent(s) as defined above.

The parenteral route of administration of the compositions as defined above generally comprises subcutaneous, intramuscular, intravenous, transdermal, intradermal, intranasal, intraarterial and intraperitoneal injection or infusion. Preferably the parenteral route comprises subcutaneous, intramuscular and intravenous injection or infusion, and more preferable the subcutaneous injection or infusion.

Further, the invention refers to the use of the above defined compositions for the preparation of medicaments useful for treatment and prevention of diseases involving bone resorption, especially osteoporosis, Paget's disease, hypercalcemia of malignancy, and metabolic bone disease.

The invention also relates to the use of the above composition for the preparation of medicaments useful for the prevention of tissue damage after parenteral administration of bisphosphonates, preferably by administration of an aqueous solution.

In addition, the invention also refers to a device for local and systemic sustained release comprising a composition as defined above. For example, such devices may consist of implanted osmotic pumps or externally portable infusion pumps connected to a supply tube and/or a subcutaneously inserted cannula.

Further, the invention also refers to a device for enabling, facilitating or supporting parenteral administration of a composition as defined above. For example, the device may be used to achieve local and systemic sustained release comprising portable infusion pumps connected to a supply tube and/or a subcutaneously inserted cannula (e.g. Portable Injection Appliance; U.S. Pat. No. 4,886,499) or to reduce local pain caused by the injection, for example needle free injectors (e.g. MicroPor™, Medi-jector™).

Further the invention also relates to injectable formulations, which release a composition as defined above in a sustained fashion and may reduce local pain caused by injection. For example, the sustained release formulation may comprise depot forming compounds such as different pharmaceutically acceptable oils, thickening agents (carboxymethylcellulose, poloxamer, gelatin), biodegradable microparticle forming polymers (lactide/glycolide polymers, polyanhydrides, chitosan) or pharmaceutically acceptable polyelectrolytes (Albumin, Protamin).

The invention will be now illustrated in details by the following examples and figures.

EXAMPLES

Example 1

Local Tolerance Test I

Figure 1:
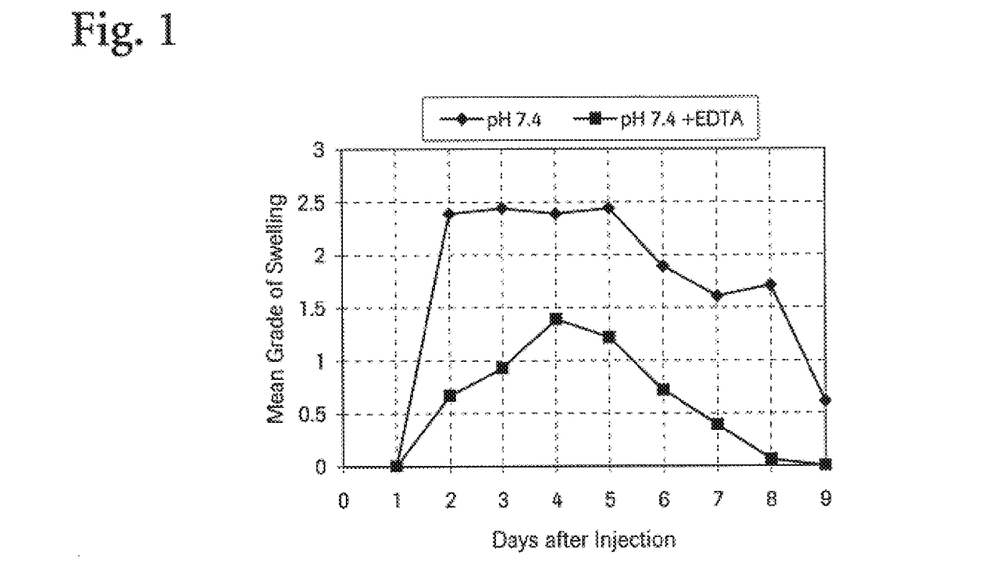
FIG. 1 depicts a graph of the mean grade of swelling after s.c. injection of ibandronate solution, pH 7.4 with and without 0.1% EDTA (n=9).
Figure 2:
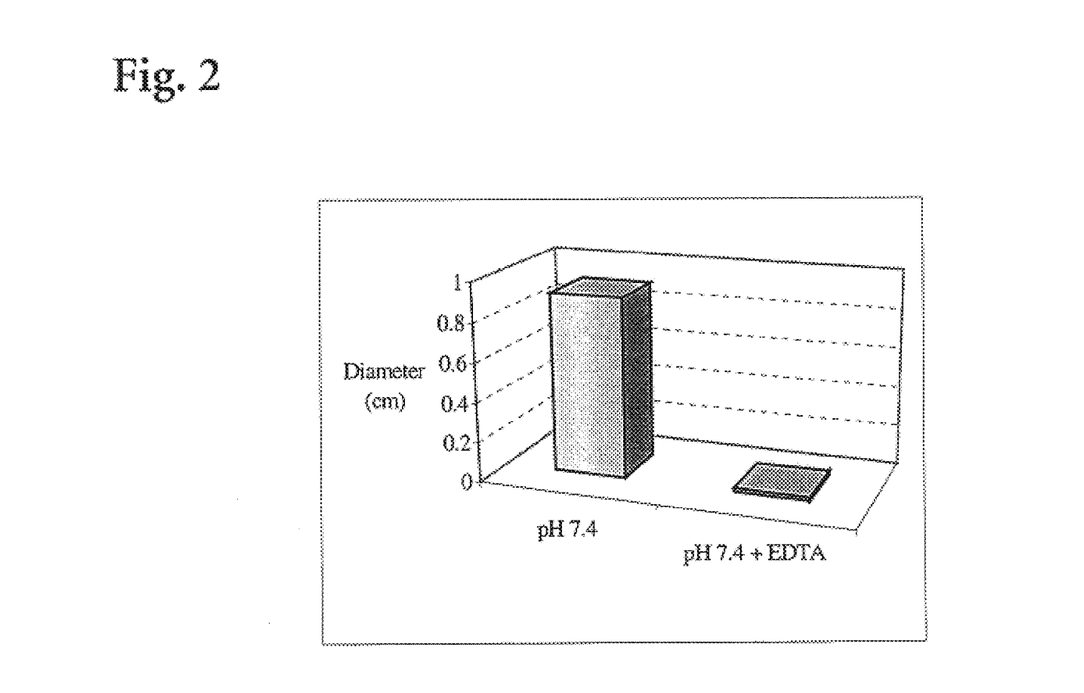
FIG. 2 depicts a bar graph of the mean diameter of subcutaneous findings 9 days after s.c. injection of ibandronate solution, pH 7.4 with and without 0.1% EDTA (n=9).

Groups of 3 rats were treated with test formulations containing 1 mg ibandronate/ml physiological saline buffered at pH 7.4. One group of rats received the test formulation without any additional additive, another group received the test solution with 1 mg EDTA/ml as an additive. The back of the rat was shaved one day before treatment. A volume of 0.5 ml each was injected subcutaneously at three different sites of the right part of shaved back. The left side of the back was treated with the corresponding formulation without ibandronate (placebo). Local reactions were assessed by a scoring system for swelling: 0=no reaction, 0.5=barely perceptible swelling, 1=slight swelling, 2=moderate swelling, 3=marked swelling, 4=severe swelling. The animals were observed over 9 days and thereafter necropsied. At necropsy, the diameter of subcutaneous lesions, mainly consisting of reddening or swelling, was measured. The results are presented in FIGS. 1 and 2.

Example 2

Local Tolerance Test II

Figure 3:
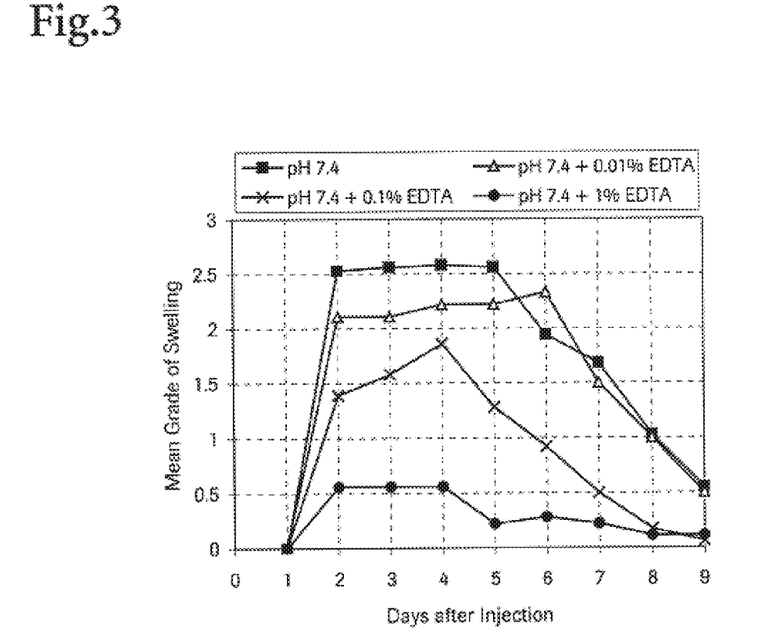
FIG. 3 depicts a graph of the mean grade of swelling after s.c. injection of ibandronate solution, pH 7.4 with and without EDTA (n=9). Data with 0.1% EDTA are combined with results of the first test (n=18).
Figure 4:
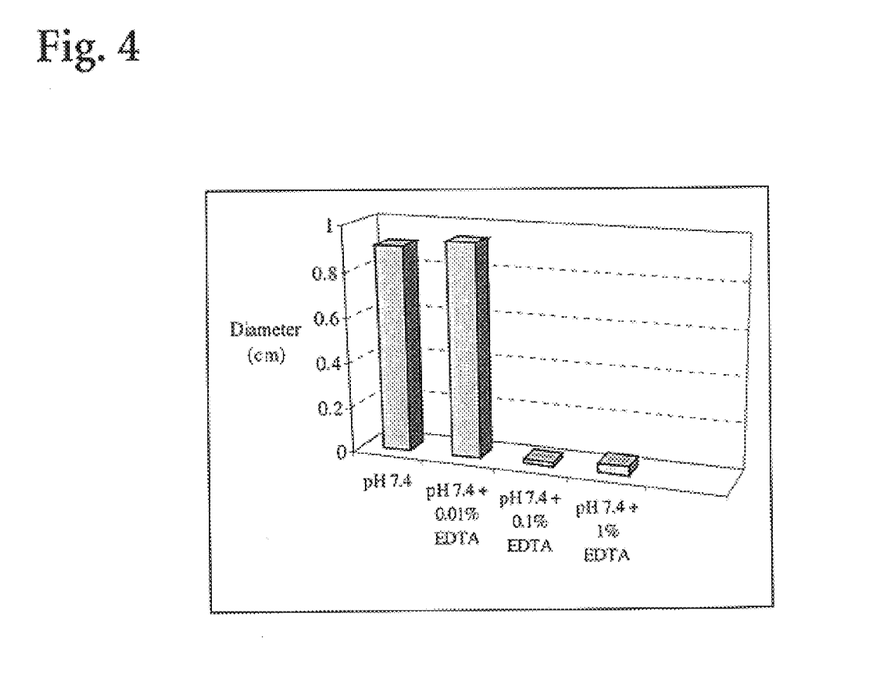
FIG. 4 depicts a bar graph of the mean diameter of subcutaneous findings 9 days after s.c. injection of ibandronate solution, pH 7.4 with and without EDTA (n=9). Data with 0.1% EDTA are combined with results of the first test (n=18).

The same study design as described in example 1 was applied to examine the concentration dependence of the EDTA effect. EDTA was added at concentrations of 0.1, 1.0 and 10 mg/ml. The results are presented in FIGS. 3 and 4.

Example 3

Local Tolerance Test III

Figure 5:
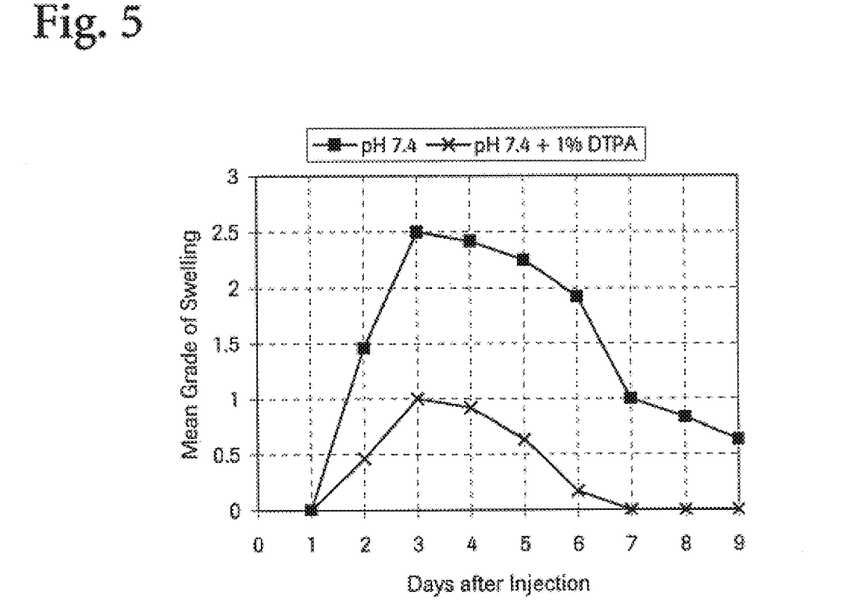
FIG. 5 depicts a graph of the mean grade of swelling after s.c. injection of ibandronate solution, pH 7.4 with and without 1% DTPA (n=12).
Figure 6:
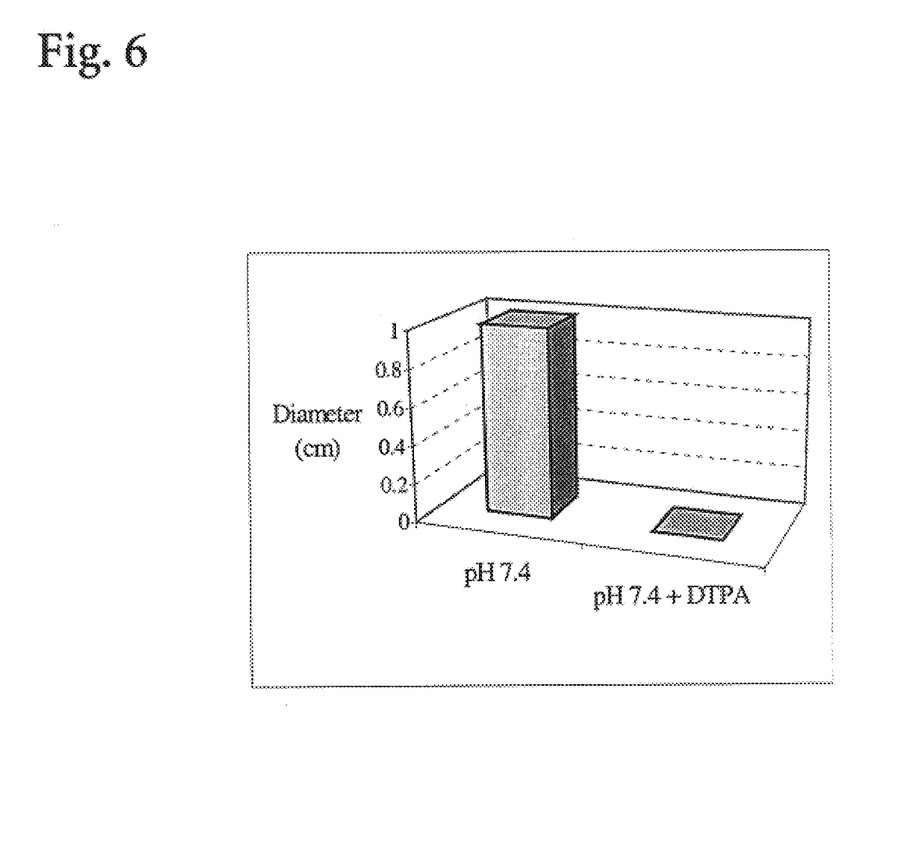
FIG. 6 depicts a bar graph of the mean diameter of subcutaneous findings 9 days after s.c. injection of ibandronate solution, pH 7.4 with and without DTPA (n=12).

The same study design as described in example 1 was applied to examine the efficacy of DTPA on local reaction to s.c. injected ibandronate. DTPA was added at a concentration of 10 mg/ml. The results are presented in FIGS. 5 and 6.

Example 4

Local Tolerance Test IV

Figure 7:
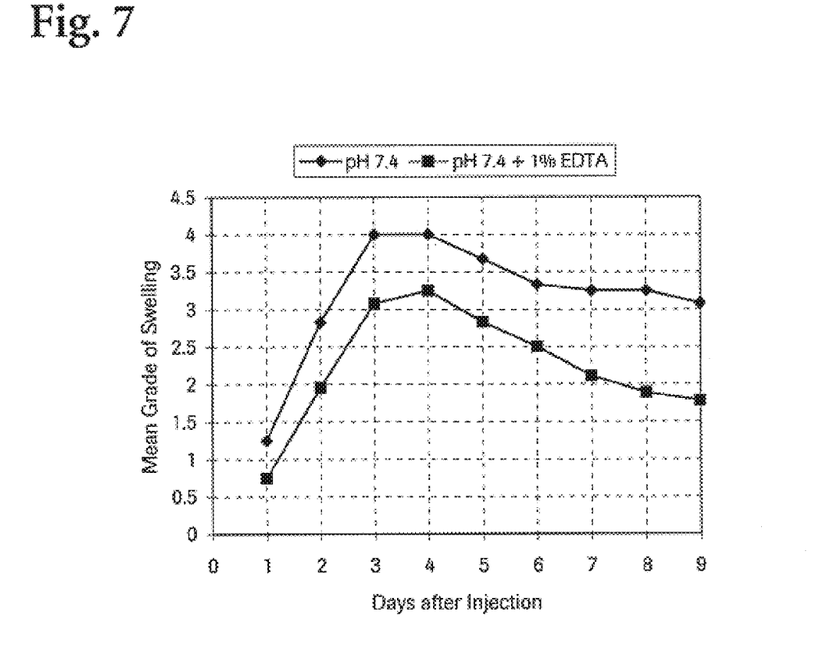
FIG. 7 depicts a graph of the mean grade of swelling after s.c. injection of alendronate solution, pH 7.4 with and without 1% EDTA (n=9).
Figure 8:
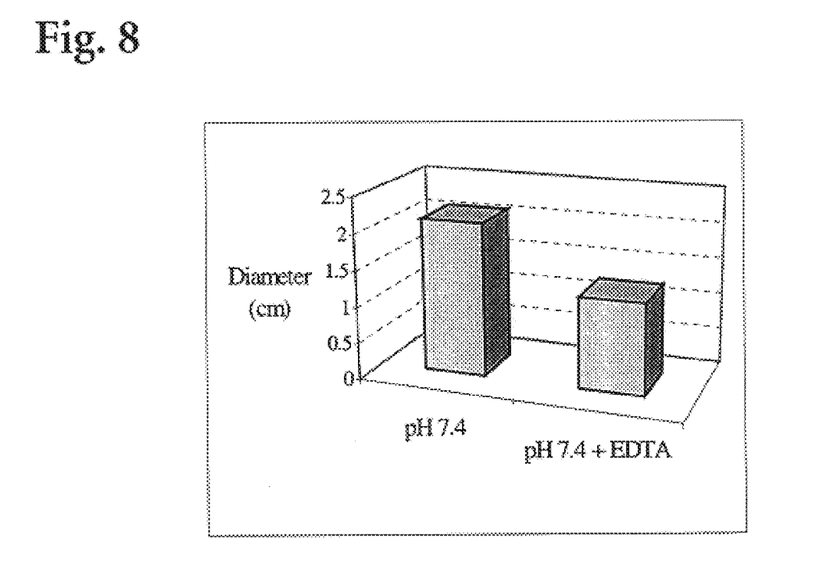
FIG. 8 depicts a bar graph of the mean diameter of subcutaneous findings 9 days after s.c. injection of alendronate solution, pH 7.4 with and without EDTA (n=9).

The same study design as described in example 1 was applied to examine the efficacy of EDTA on local reaction to s.c. injected alendronate. The test formulations contained 3 mg alendronate/ml physiological saline buffered at pH 7.4. EDTA was added at a concentration of 10 mg/ml. The results are presented in FIGS. 7 and 8.

In conclusion, there is clear evidence that the presence of a chelating agent, as EDTA or DTPA, in injectable formulations of bisphosphonates, as alendronate or ibandronate, reduces both the intensity and duration of local swelling at the injection site and the severity of subcutaneous findings at necropsy after 9 days.

Example 5

Parenteral Composition I

| | | |
|---|---|---|
| Ibandronate sodium salt | 1.125 | mg |
| EDTA, Na$_2$, 2H$_2$O | 10.0 | mg |
| Sodium chloride | 9.0 | mg |
| Sodium hydroxyde q.s. to | pH 7.4 | |
| Water for Injection q.s. to | 1.0 | ml |

Example 6

Parenteral Composition II

| | | |
|---|---|---|
| Ibandronate sodium salt | 1.125 | mg |
| DTPA | 10.0 | mg |
| Sodium chloride | 9.0 | mg |
| Sodium hydroxyde q.s. to | pH 7.4 | |
| Water for Injection q.s. to | 1.0 | ml |

Example 7

Parenteral Composition III

| | | |
|---|---|---|
| Alendronate | 3.0 | mg |
| EDTA, Na$_2$, 2H$_2$O | 10.0 | mg |
| Sodium chloride | 9.0 | mg |
| Sodium hydroxyde q.s. to | pH 7.4 | |
| Water for Injection q.s. to | 1.0 | ml |

Example 8

Parenteral Composition IV

| | | |
|---|---|---|
| Ibandronate sodium salt | 1.125 | mg |
| EDTA, Na$_2$, 2H$_2$O | 10.0 | mg |
| Lidocaine hydrochloride | 5.78 | mg |
| Sodium chloride | 9.0 | mg |

| | | |
|---|---|---|
| Sodium hydroxyde q.s. to | pH 7.4 | |
| Water for Injection q.s. to | 1.0 | ml |

What is claimed is:

1. A method for the treatment and prevention of diseases involving bone resorption, osteoporosis, Paget's disease, hypercalcemia of malignancy, and metabolic bone disease comprising the step of administering to a patient in need of such treatment and prevention a parenteral composition having a pH of from about 6 to about 8 comprising a pharmaceutically acceptable bivalent cation chelating agent and at least one bisphosphonate selected from the group consisting of
   a) N-methyl-4-amino-1-hydroxybutylidene-1,1-bisphosphonic acid,
   b) 4-(N,N-dimethylamino)-1-hydroxybutylidene-1,1-bisphosphonic acid,
   c) 3-amino-1-hydroxypropylidene-1,1-bisphosphonic acid,
   d) 3-(N-methyl-N-pentyl)amino-1-hydroxypropane-1,1-bisphosphonic acid,
   e) 3-(N-methyl-N-pentyl)amino-1-hydroxypropane-1,1-bisphosphonic acid,
   f) 1-hydroxy-3-(N-methyl-N-pentylamino)propylidene-1,1-bisphosphonic acid,
   g) 1-hydroxy-2-[3-pyridinyl]ethylidene-1,1-bisphosphonic acid,
   h) 4-(hyroxymethylene-1,1-bisphosphonic acid) piperidine,
   i) cycloheptylaminomethylene-1,1-bisposphonic acid,
   j) 1,1-dichloromethylene-1,1-diphosphonic acid,
   k) 1-hydroxy-3-(1-pyrrolidinyl)-propylidene-1,1-bisphosphonic acid,
   l) 1-hydroxyethane-1,1-ciphosphonic acid,
   m) 6-amino-1-hydroxyhexylidene-1,1-bisphosphonic acid,
   n) 3-(dimethylamino)-1-hydroxypropylidene-1,1-bisphosphonic acid,
   o) [2-(2-pyridinyl)ethylidene]-1,1-bisphosphonic acid,
   p) (4-chlorophenyl)thiorrethane-1,1-diphosponic acid,
   q) 1-hydroxy-2-(1H-imidazol-1-yl)ethylidene-1,1-bisphosphonic acid,
   r) [(cycloheptylamino)-methylene]-bisphosphonic acid, and
   s) 1-hydroxy-2-imidazo-(1,2-a)pyridin-3-ylethylidene]-bisphosphonic acid and pharmaceutically acceptable salts thereof wherein the molar ratio between the bisphosphonate and the chelating agent is from about 1:0.1 to about 1:50.

2. A method for the treatment or prevention of bone loss associated with a disease resulting in bone resorption comprising parenterally administering to a patient in need of such treatment and prevention an effective amount of a composition comprising a bivalent cation chelator and a bisphosphonate compound selected from the group consisting of
   a) N-methyl-4-amino-1-hydroxybutylidene-1,1-bisphosphonic acid,
   b) 4-(N,N-dimethylamino)-1-hydroxybutylidene-1,1-bisphosphonic acid, c) 3-amino-1-hydroxypropylidene-1,1-bisphosphonic acid,
d) 3-(N-methyl-N-pentyl)amino-1-hydroxypropane-1,1-bisphosphonic acid,
e) [-3-(N-methyl-N-pentyl)amino-1-hydroxypropane-1,1-bisphosphonic acid,
f) 1-hydroxy-3-(N-methyl-N-pentylamino)propylidene-1,1-bisphosphonic acid,
g) 1-hydroxy-2-[3-pyridinyl]ethylidene-1,1-bisphosphonic acid,
h) 4-(hyroxymethylene-1,1-bisphosphonic acid) piperidine,
i) cycloheptylaminomethylene-1,1-bisposphonic acid,
j) 1,1-dichloromethylene-1,1-diphosphonic acid,
k) 1-hydroxy-3-(1-pyrrolidinyl)-propylidene-1,1-bisphosphonic acid,
l) 1-hydroxyethane-1,1-diphosphonic acid,
m) 6-amino-1-hydroxyhexylidene-1,1-bisphosphonic acid,
n) 3-(dimethylamino)-1-hydroxypropylidene-1,1-bisphosphonic acid,
o) [2-(2-pyridinyl)ethylidene]-1,1-bisphosphonic acid,
p) (4-chlorophenyl)thiomethane-1,1-diphosponic acid,
q) 1-hydroxy-2-(1H-imidazol-1-yl)ethylidene-1,1-bisphosphonic acid,
r) [-(cycloheptylamino)-methylene]-bisphosphonic acid, and
s) 1-hydroxy-2-imidazo-(1,2-a) pyridin-3-ylethylidene]-bisphosphonic acid and pharmaceutically acceptable salts thereof, said composition having a pH of from about 6 to about 8 and wherein the molar ratio between the bisphosphonate and the chelator is from about 1:0.1 to about 1:50.

* * * * *

UNITED STATES PATENT AND TRADEMARK OFFICE
CERTIFICATE OF CORRECTION

PATENT NO. : 6,677,320 B2
DATED : January 13, 2004
INVENTOR(S) : Anke Diederich, Pierre Goldbach and Thomas Pfister

It is certified that error appears in the above-identified patent and that said Letters Patent is hereby corrected as shown below:

Title page,
Item [73], Assignee, delete "Hoffmann-La Roches Inc., Nutley, NJ (US)" and insert
-- Hoffmann-La Roche Inc., Nutley, NJ (US) --.

Column 10,
Line 39, delete "l) 1-hydroxyethane-1,1-ciphosphonic acid," and insert
-- l) 1-hydroxyethane-1, 1-diphosphonic acid, --.
Line 46, delete "p) (4-chlorophenyl)thiorrethane-1,1-diphosponic acid," and insert
-- p) (4-chlorophenyl)thiomethane-1,1-diphosponic acid, --.
Line 51, delete "s) 1-hydroxy-2-imidazo-(1,2-a) pyridin-3-ylethylidene]-" and
insert -- s) 1-hydroxy-2-imidazo-(1,2-a) pyridin-3-ylethylidene- --.

Signed and Sealed this

Twelfth Day of October, 2004

JON W. DUDAS
*Director of the United States Patent and Trademark Office*